United States Patent [19]

Lare

[11] 4,410,325
[45] Oct. 18, 1983

[54] DIAPER TAB SEPARABLE AND REJOINABLE AT AN ADHESIVE INTERFACE

[75] Inventor: Donald W. Lare, Perry, Ohio

[73] Assignee: Avery International Corporation, Pasadena, Calif.

[21] Appl. No.: 232,151

[22] Filed: Feb. 6, 1981

[51] Int. Cl.³ .............................................. A41B 13/02
[52] U.S. Cl. ...................................................... 604/389
[58] Field of Search .............. 128/284, 287, DIG. 30; 428/343, 354, 355; 604/389–390

[56] References Cited

U.S. PATENT DOCUMENTS

| | | | |
|---|---|---|---|
| 3,257,228 | 6/1966 | Reed | 428/354 |
| 4,020,842 | 5/1977 | Richman et al. | 128/DIG. 30 |
| 4,112,177 | 9/1978 | Salditt et al. | 428/355 |
| 4,178,933 | 12/1979 | Nemeth | 128/DIG. 30 |
| 4,186,744 | 2/1980 | Ness | 128/287 |

Primary Examiner—C. Fred Rosenbaum
Attorney, Agent, or Firm—Pearne, Gordon, Sessions, McCoy, Granger & Tilberry

[57] ABSTRACT

A reclosable fastening tab for diapers or the like forms an adhesive interface at an intermediate location within the thickness of the adhesive at the "user end" of the tab when the tab is unfastened after originally being fastened by the user. The adhesive on one side of the interface remains with the portion of the diaper to which the user end of the tab was fastened and the adhesive on the other side of the interface remains with the user end of the tab.

1 Claim, 14 Drawing Figures

DIAPER TAB SEPARABLE AND REJOINABLE AT AN ADHESIVE INTERFACE

This invention relates to tabs for disposable diapers or geriatric briefs or the like.

In the manufacture of disposable diapers, it is typical practice for the diaper manufacturer to provide diaper tabs fixed to the diaper proper. Each tab is permanently attached at its "factory end" to the diaper and its other "user end" is then later fastened to another part of the diaper by the parent or other user who purchases and utilizes the diaper. The user end is provided with a pressure-sensitive adhesive which is suitably protected prior to use. The user manipulates the user end to expose the adhesive and then presses the user end and its exposed adhesive against a receiving portion of the diaper to accomplish the original fastening of the diaper.

A parent or other user will frequently wish to temporarily open a diaper in order to inspect it and then continue its use if it is still clean and dry, or in order to adjust it. For these purposes, the diaper tab must be capable of unfastening and refastening, and there is therefore a demand for diaper tabs with this capability.

The adhesive at the user end of the tab must firmly adhere to the receiving portion of the diaper proper, which is usually a plastic film, but in order for the tab to be unfastenable, the adhesive must at the same time be removable with reasonable ease from the same receiving plastic film. These two requirements are, of course, inconsistent and require that the formulation of the adhesive be matched to bonding and release characteristics of the particular receiving plastic film used in the diaper. For the satisfactory accomplishment of such matching, it is not enough that bonding and release characteristics be satisfactory following application of the tab at some "normal" or standard pressure by a parent or other user. Sensitivity to pressure of application must also be investigated. For a particular adhesive and diaper material, bonding and release may be satisfactory when an intermediate "normal" pressure of application is used, but sensitivity to pressure of application may be too high, so that, on the one hand, only a relatively slight decrease in pressure of application makes release so easy that the tab does not hold but, on the other hand, only a relatively slight increase in pressure of application makes release so difficult that, when unfastening is attempted, the plastic diaper film is torn. Accordingly, proper matching requires selection of an adhesive that, for the particular diaper material, will have acceptable bonding and release characteristics over a reasonably broad range of pressures of application.

This requirement that tabs be matched to diapers in respect of adhesive performance is particularly significant in view of the fact that the adhesive-coated stock from which tabs are formed in typically purchased by diaper manufacturers from other companies who specialize in the kinds of web converting and coating operations that make possible the efficient production of such tab stock. The matching requirement means that a tab stock manufacturer must be requested by the diaper manufacturer to especially tailor the tab adhesive to the particular plastic film used by the diaper, thus tending to increase costs.

Several approaches have been used to avoid the problem of matching. One is to provide multiple substrates each with its own adhesive coating, as in Richman et al. U.S. Pat. No. 4,020,842 and Nemeth U.S. Pat. No. 4,111,205. Another is to provide a transferring adhesive coating, as in Nemeth U.S. Pat. No. 4,178,933, all of common assignee. In these constructions, the parting interface upon reopening is different from the adhesive-to-diaper interface upon original closing. However, the first two of these constructions require additional substrate layers and the third relies for reclosed adhesion on the reclosing of an interface between an adhesive and a release coat which is not always satisfactory.

The present invention does not require additional substrates, does not rely for reclosing adhesion on the reclosing of an interface between an adhesive and a release coat, and nevertheless avoids the necessity for specific matching between the adhesive of the tab stock and the receiving plastic of the diaper and for specific evaluation of their sensitivity to pressure of application.

The invention provides a tab which forms an intraadhesive cleavage face, that is, an adhesive interface at an intermediate location within the thickness of the adhesive at the user end of the tab, when the tab is unfastened after originally being fastened by the user. The adhesive on one side of the cleavage face remains with the portion of the diaper to which the user end of the tab was fastened, and the adhesive on the other side of the cleavage face remains with the user end of the tab. Upon reclosing, the two portions of adhesive are again joined at the cleavage face. The adhesive at the user end of the tab may comprise a single layer or two adjacent layers of unlike adhesive. In either case, the adhesive as a whole is selected to adhere more strongly to the receiving plastic film on the diaper than it does to itself.

The invention may be more specifically described in connection with the accompanying drawings, in which the thicknesses of the webs and coatings are greatly exaggerated.

Figure 1:
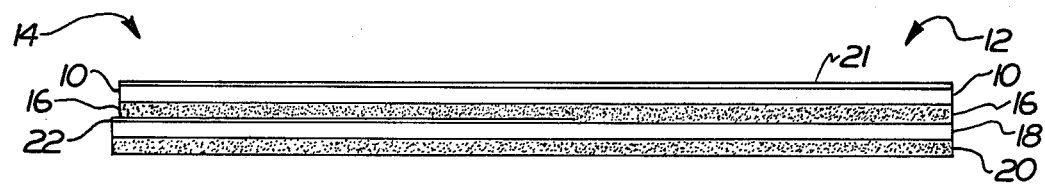
FIG. 1 is a schematic, transverse elevation of diaper tab stock constructed according to the invention and then cut transversely to machine direction (machine direction being directly into the surface of the page) into an individual diaper tab laminate.

The diaper tab shown in FIGS. 1–5 has a principal substrate 10 having a "machine end" 12 and a "user end" 14. Adhesive means for the principal substrate 10 is provided in the form of a single adhesive layer 16. At the factory end 12, this adhesive means 16 is permanently associated throughout the thickness of the adhesive with the principal substrate 10, and permanently applies the factory end of the principal substrate 10 to a first portion D1 (FIGS. 2-5) of a diaper. In the particular embodiment illustrated, such permanent application is accomplished via a secondary substrate 18 and secondary substrate adhesive 20, the elements 10, 16, 18, and 20 remaining permanently associated with each other at all times, and remaining permanently associated with the portions D1 of the diaper once the adhesive 20 is applied directly thereto as seen in FIGS. 2-5.

Figure 4:
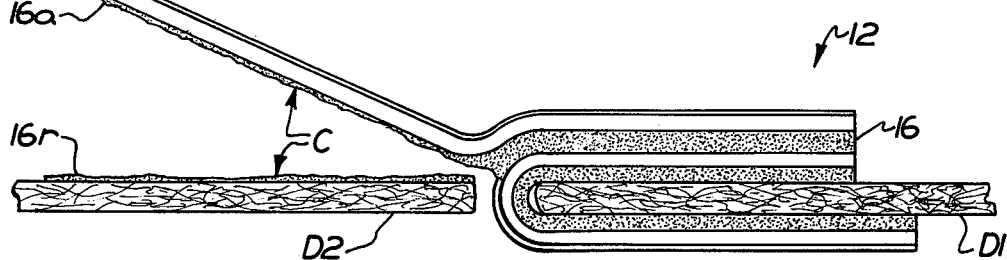
FIG. 4 is a view showing the configuration of the parts as the diaper tab is initially unfastened following its initial fastening.
Figure 5:
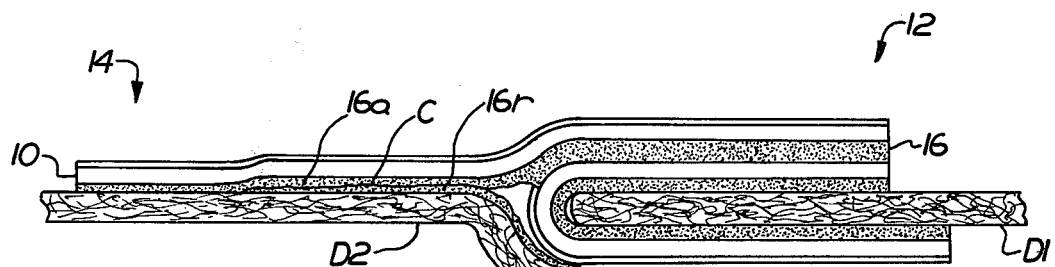
FIG. 5 is a view showing a configuration of the parts when the diaper tab is subsequently refastened.

At the user end 14, the adhesive means 16 provides means for temporarily applying the user end 14 of the principal substrate 12 to a receiving film on the surface of a second diaper portion D2 (FIG. 3) and for allowing removal of said user end from said second portion to thereby unfasten the tab (FIG. 4), and for then reapplying said user end to said second portion to thereby refasten the tab (FIG. 5).

Figure 2:
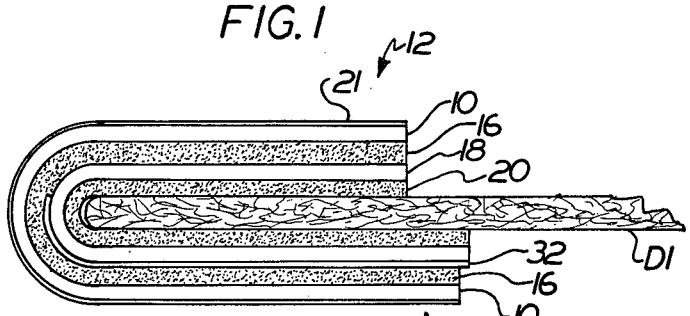
FIG. 2 is a view of the laminate seen in FIG. 1 as folded and fastened at one edge of one portion of a diaper by the diaper manufacturer.
Figure 3:
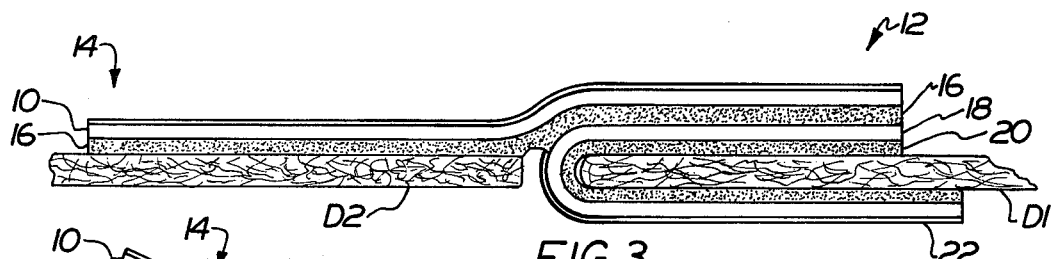
FIG. 3 is a view of the same laminate, now unfolded and with the user end applied and joined to the receiving plastic at another portion of the diaper.

Prior to application of the user end 14 of the tab to the portion D2 of the diaper, the user end is stored around an edge of the diaper portion D1 as seen in FIG. 2. The adhesive means 16 at the user end is temporarily stored against a release coat 22 which, as illustrated, is coated on only the portion of the secondary substrate 18 which is associated with the user end 14. This protects the adhesive means 16 until the user end of the tab is peeled away from the release coat 22 to be applied to the second diaper portion D2.

The principal substrate adhesive means 16 at the user end 14 is permanently associated with the principal substrate 10 only throughout the adjacent portion 16a (FIGS. 4,5) of the entirety of the thickness of adhesive means 16, and is disassociatable throughout the remote remaining portion 16r (FIGS. 4,5) of the entirety of the thickness of adhesive means 16 by self-division along an intra-adhesive cleavage interface C (FIGS. 4,5). In this embodiment of the invention, the principal substrate adhesive means 16 at the user end 14 has a greater affinity for both the receiving plastic of the diaper portion D2 and for the principal substrate 10 than for itself, thus causing the self-division as illustrated in FIG. 4. The portion of adhesive thickness 16r that is remote to the principal substrate 10 in effect transfers to the diaper portion D2 when the tab is unfastened as in FIG. 4, and provides a landing zone on the diaper portion D2.

The adhesive means 10 at the user end is rejoinable to itself at the cleavage interface C to effect refastening of the tab. If the diaper is tightened or stretched by the parent during reapplication, the user end 14 of the tab may extend further along the diaper portion D2 than originally and the tab may overlap beyond the landing zone 16r. Nevertheless, a good bond is re-established at the reconstituted interface C and the strength of the fastening may be somewhat strengthened by the direct adhesion between 16a and D2. The tab may be subsequently reopened and reclosed in a similar manner with good bonding at the remaining portion of the interface C. On such a subsequent opening, the layer 16a may itself divide to form another reclosable intra-adhesive cleavage face or interface (not shown) toward the free end of the user end of the tab if the adhesive body is of sufficient thickness.

A release coat 21 (FIG. 1) may be provided on the outside of the principal substrate 10 to allow self-winding of the adhesive 20 against the outside of the substrate for storage and shipment prior to the cutting of the tab stock into individual diaper tabs.

In the embodiment of FIGS. 6-10, the principal substrate 30 has factory and user ends 32 and 34 and is provided with an adhesive layer 36 at its factory end for directly permanently associating the principal substrate 30 with a first diaper portion D2. The adhesive means at the user end comprises an extension of the adhesive layer 36 which, at the user end, is labeled 36a. A separate adhesive layer 36r is provided over the layer 36a at the user end.

Figure 6:
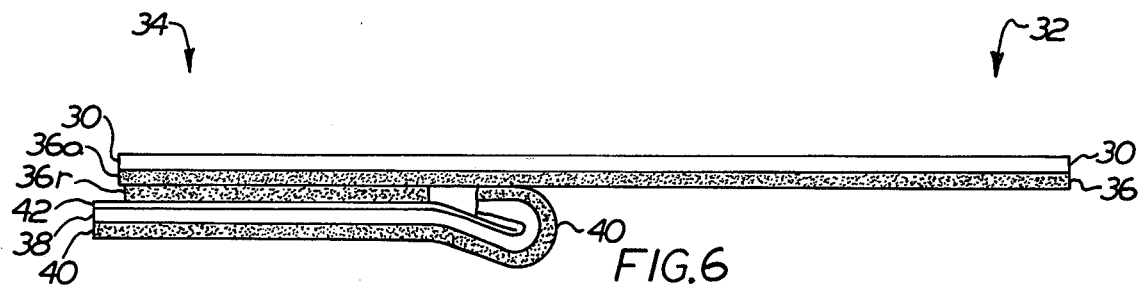
FIGS. 6 to 10 show another form of diaper tab construction employing the invention, and correspond to the stages shown in FIGS. 1 to 5, respectively.
Figure 7:
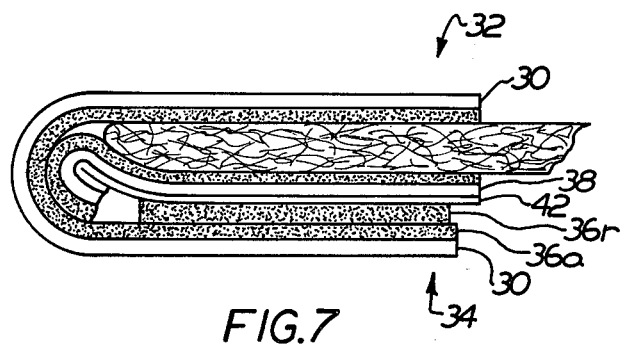
Figure 8:
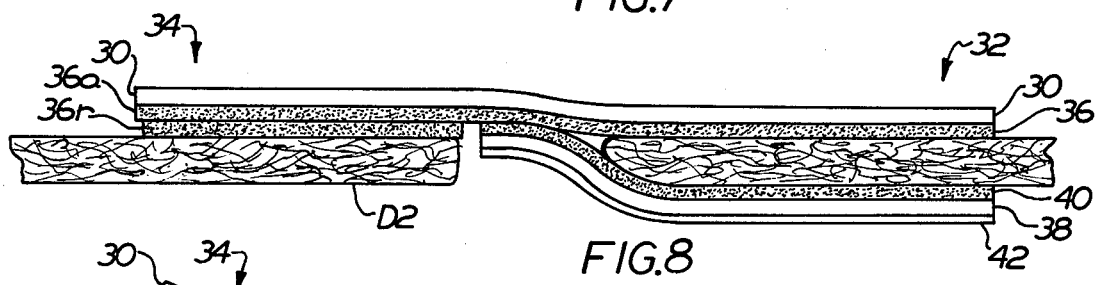
Figure 9:
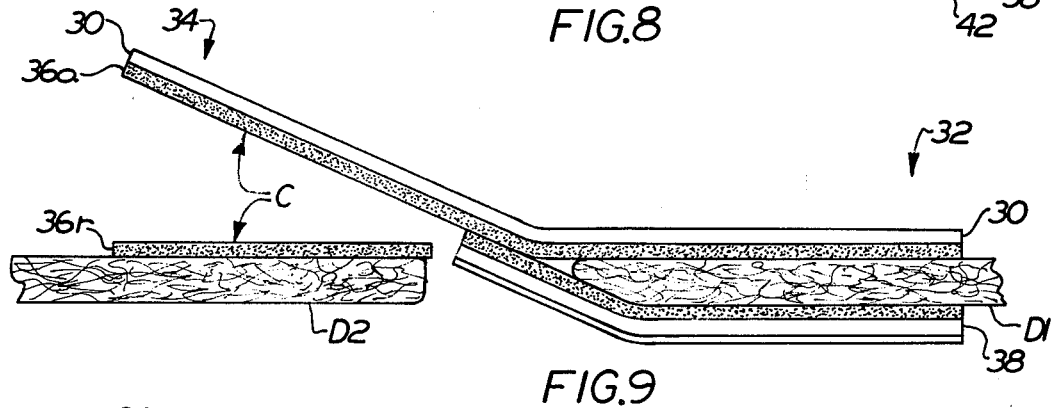
Figure 10:
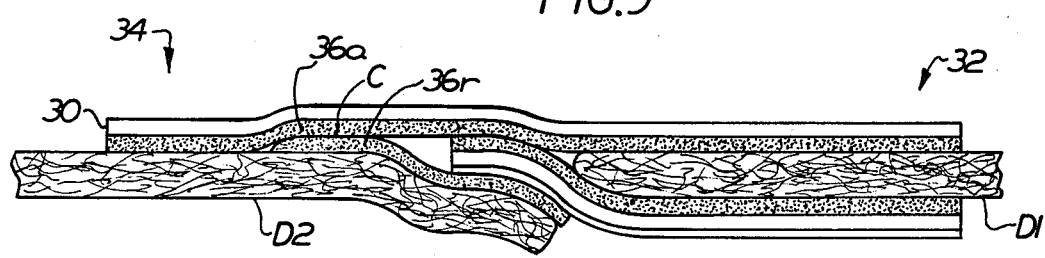

Prior to factory installation of the tab on the diaper portion D1, the primary substrate 30 is combined with a secondary substrate 38 which is provided with a release coat 42 against which the outer face of adhesive 36r is protected during storage. Prior to application of the user end 34 of the tab to the portion D2 of the diaper, the user end is stored around an edge of the diaper portion D1, as seen in FIG. 7, and rests against the release coat 42 on the secondary substrate 38. The secondary substrate 38 is permanently adhered to the diaper portion D1 by secondary substrate adhesive 40, being fixed on the side of D1 which is opposed to the side to which the principal substrate 30 is permanently fixed at the factory end 32. A strong joint between the principal substrate 30 and the secondary substrate 38 is formed at a point between the factory and user ends where the secondary substrate is folded back on itself to expose the secondary substrate adhesive 40 directly to the principal substrate adhesive 36, as shown in FIGS. 6 and 7. When the user end is deployed, as in FIGS. 8-10, this joint becomes the branching portion of a Y-configuration fastener adhered to both sides of the diaper portion D1.

The principal substrate adhesive means at the user end 34 is permanently associated with the principal substrate 30 only throughout the adjacent portion 36a of the entirety of the thickness of the adhesive means at the user end, and is disassociatable throughout the remote remaining portion 36r of the entirety of the thickness of the adhesive means at the user end (portions 36r being in this instance a separate layer of adhesive) by self-division along an intra-adhesive cleavage interface C. The adhesive 36r is selected to adhere more strongly to the receiving plastic of the diaper portion D2 than the bond between 36a and 36r. Adhesive 36a may, if desired, be selected to have a very weak affinity for the receiving plastic of diaper portion D2 so that even when there is user end overlap upon diaper reclosing, as in FIG. 10, there is no possibility of a problem of tearing of the receiving film upon subsequent tab reopening. The transferring adhesive 36r may serve to reinforce the receiving plastic at the landing zone established by adhesive 36r when it transfers.

Figure 11:
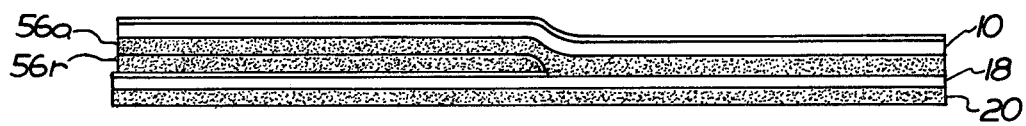
FIGS. 11 and 12 show still another form of diaper tab construction employing the invention, and correspond to the stages shown in FIGS. 1 and 5, respectively.
Figure 12:
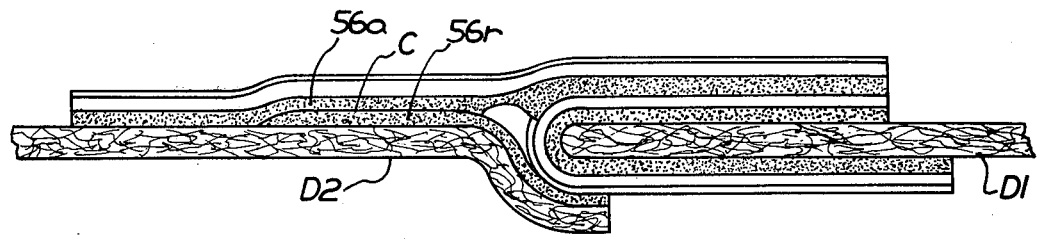

The embodiment of FIGS. 11 and 12 is generally similar to that of FIGS. 1-5, except that the single self-dividing adhesive means 16 at the user end of FIGS. 1-5 is replaced by the separate adhesive layers 56a and 56r, similar to the layers 36a and 36r in FIGS. 6-10.

Figure 13:
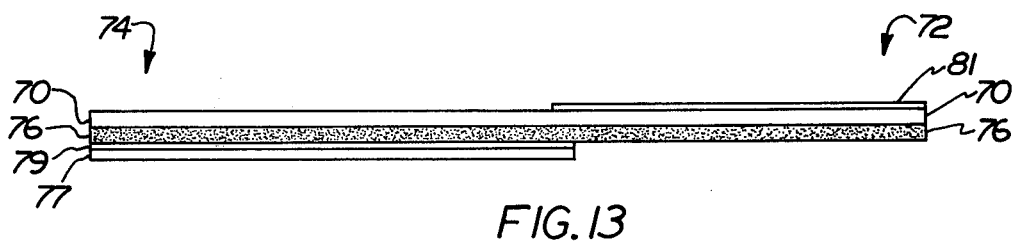
FIGS. 13 and 14 show one more form of diaper tab construction employing the invention and, in a broad sense, can also be said to correspond to the stages shown in FIGS. 1 and 5.
Figure 14:
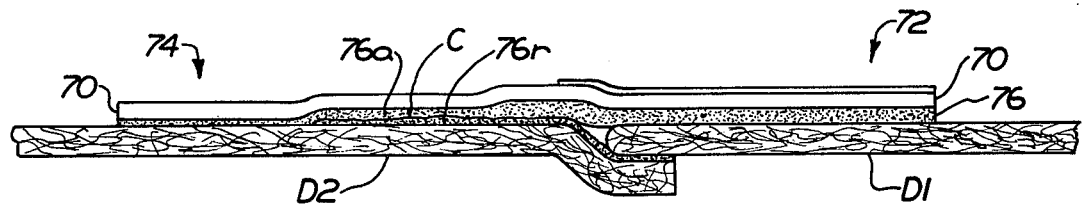

In the embodiment of FIGS. 13 and 14, a principal substrate 70 is the only substrate of the construction. Adhesive means 76 is similar to the adhesive means 16 of FIGS. 1-5. At the factory end 72, the adhesive 76 permanently attaches the tab to diaper portion D1 (FIG. 14). At the user end 74, the adhesive means 76 is protected prior to application to diaper portion D2 by a release liner 77 bearing a release coat 79 (FIG. 13). The release liner 77 is discarded by the user after removal at the time the diaper is originally applied and fastened.

A release coat 81 may be provided at the factory end of the tab to allow self-winding of the adhesive 76 against the outside of the substrate 70 for storage and shipment prior to the cutting of the tab stock into individual diaper tabs.

The tab of FIGS. 13 and 14 is never stored around the edge of a diaper. Prior to application of the diaper by the user, the user end 74 is simply allowed to project from the diaper edge, with the adhesive means 56 protected by the liner 77.

At the user end 74, the principal substrate adhesive means 76 is permanently associated with the principal substrate 70 only throughout the adjacent portion 76a (FIG. 14) of the entirety of the thickness of adhesive means 76. By self-division along the intra-adhesive cleavage interface C, the portion of adhesive thickness 76r that is remote to the principal substrate 70 transfers to the diaper portion D2 when the tab is initially unfastened. Again, this is accomplished by providing an adhesive which has a greater affinity for both the receiving plastic of the diaper portion D2 and for the principal substrate 70 than for itself, thus causing the self-division at the intra-adhesive cleavage interface C.

All embodiments as described have included one adhesive layer which continues from end to end of the tab, so that for example in FIG. 1 the same adhesive means 16 is employed for permanently fastening the factory end 12 and temporarily and releasably fastening the user end 14, and in FIG. 6 the same layer 36 is employed for permanently fastening the factory end and as part of the temporary and releasable fastening system at the user end. However, it is also intended that the principal substrate may be pattern coated with different adhesives at the factory and user ends, so that no common adhesive and no common adhesive layer is shared by the factory and user ends.

The constructions where two different adhesives are provided at the user end, as in FIGS. 6-10 and FIGS. 11 and 12, are presently preferred. The adhesive portions 36a or 56a can each be referred to as a non-transferring adhesive, since each remains permanently associated with the substrate with which it is originally associated. Correspondingly, the adhesive portion 36r or 56r can each be referred to as a transferring adhesive. While specific adhesive formulations form no part of this invention, it may be stated that the non-transferring adheisve can be a high cohesive strength, pressure-sensitive adhesive, such as an adhesive of the cross-linked acrylic type. It presently appears that the adhesive should have relatively low peel adhesion, for example, less than 1 pound per inch width, to stainless steel, typical of many "removable" pressure-sensitive adhesives. The transferring adhesive can be a rubber-base adhesive which will have good adhesion to the polyethylene film typically used as the outer layer of the disposable diaper, typically di-, tri-, and radical block copolymers of styrene and rubbers such as isoprene or butadiene, as well as natural rubber. To such base rubbers are added various tackifying resins such as rosin, rosin derivatives, and hydrocarbon resins. As an example, "Kraton 1107" (styrene-isoprene-styrene) block copolymer, supplied by Shell Chemical Company, can be mixed with hydrogenated rosin ester and polymerized rosin ester tackifiers, either in solvent or as a hotmelt, to form the transferring adhesive. The primary requirement of the transferring adhesive is that its specific adhesion to even the most weakly bonding film of the entire range of diaper films which may be encountered be greater than its specific adhesion to the non-transferring adhesive. It is also necessary that intra-adhesive bond force be less than the force necessary to tear the diaper film, or at least less than the force necessary to tear the diaper film reinforced by the transferring adhesive.

The embodiment of FIGS. 1-5 uses an adheisve that may be referred to as "splittable." Such adhesives are known in the pressure-sensitive adhesive art and are obtainable by taking almost any elastomer and adding plasticizers and tackifiers to lower the cohesive strength and/or increase the adhesive strength of the elastomer to the substrates to the point at which adhesion exceeds cohesion. In the present instance, the adhesive prepared must have adhesion to the principal substrate 30 and to even the most weakly bonding film to be encountered that exceeds the cohesive strength of the adhesive.

The adhesive layers may either be directly applied to their respective substrates or they may be transferred from suitable carriers such as release liners (not shown) in a known manner. For example, coating 36 in FIG. 6 may be directly applied to substrate 30 and then coating 36r may be transferred into its illustrated association with coating 36a and substrate 30 from a release liner (not shown) which is then removed prior to the combining of substrate 38 into the construction.

The overall construction may be other than those shown in the above-described specific embodiments. For example, in still another modification, the invention may be incorporated in an overall construction of the type shown in Richman U.S. Pat. No. 4,050,121, whose disclosure is adopted by reference herein. In such modification, the construction shown in Richman is used and may be the same as Richman in all respects except that the lengthwise portion of Richman's "adhesive coating 17c" that is at the "fifth length portion" of Richman's substrate 10 (i.e., the portion of Richman's "adhesive coating 17c" that is at the user end of his construction) is formed as a self-dividing and rejoinable adhesive means such as any of the adhesive means 16, 36, 56, or 76 referred to hereinabove.

It should be evident from the foregoing that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A refastenable tab having at least a principal substrate having a "factory end" at which the tab is factory-applied by the manufacturer of diapers or the like to a first portion of a diaper or the like and a "user end" at which the tab is user-applied to a second portion of the diaper or the like to fasten or refasten the tab, principal substrate adhesive means at said factory end permanently associated, throughout the entirety of the thickness of said adhesive means, with said principal substrate at said factory end for permanently applying said factory end of said substrate to said first portion of a diaper or the like, and principal substrate adhesive means at said user end for temporarily manually applying said user end to said second portion of a diaper or the like by an initial manual application of pressure at an arbitrary level within a range to thereby fasten the tab by pressure-sensitively joining the adhesive means to said second portion along an interface between the adhesive means and said second portion, and for allowing manual removal of said user end from said second portion to thereby unfasten the tab by separation of said adhesive means from itself along an intra-adhesive cleavage interface, and for then manually reapplying said user end to said second portion by manual reapplication of pressure to thereby refasten the tab along said intra-adhesive cleavage face, and for allowing repeating of said unfastening and refastening along said intra-adhesive cleavage face as desired, said principal substrate adhesive means at said user end being permanently associated throughout only the adjacent portion of the entirety of the thickness of said adhesive means, with said principal substrate at said user end, and being disassociateable, throughout the remote remaining portion of the entirety of the thickness of said principal substrate adhesive means at said user end, from said principal substrate at said user end by self-division of said principal substrate adhesive means along said intra-adhesive cleavage interface to effect said unfastening of the tab and complete an entirely manually effected transfer, to a "landing zone" on said second portion of the diaper or the like, of said remote remaining portion of the entirety of the thickness of said principal substrate adhesive means at said user end, said adhesive means being rejoinable to itself at said intra-adhesive cleavage interface by said manual reapplication of pressure to effect said refastening of the tab, whereby the peel strength and degree of controlled and overcomeable resistance to unfastening of the user end of the tab upon both fastening and refastening of the tab is established by the tap manufacturer independently of the level of pressure of initial application and of any relatively high degrees of bond between the adhesive means and the particular material of said second portion of the diaper or the like and without reliance for reclosed adhesion on the reclosing of an interface between an adhesive and a release coat, said principal substrate adhesive means at the user end consisting of a single layer of adhesive.

* * * * *